(12) United States Patent
Tan et al.

(10) Patent No.: US 8,708,964 B2
(45) Date of Patent: *Apr. 29, 2014

(54) FLASHBACK BLOOD COLLECTION NEEDLE WITH NEEDLE SHIELD

(75) Inventors: Alvin Chee Leong Tan, Singapore (SG); Jon Yaohan Moh, Singapore (SG)

(73) Assignee: BD Medical Products, PTE. Ltd., Singapore (SG)

( * ) Notice: Subject to any disclaimer, the term of this patent is extended or adjusted under 35 U.S.C. 154(b) by 70 days.

This patent is subject to a terminal disclaimer.

(21) Appl. No.: 13/018,836

(22) Filed: Feb. 1, 2011

(65) Prior Publication Data

US 2011/0125102 A1    May 26, 2011

Related U.S. Application Data

(63) Continuation of application No. 11/609,702, filed on Dec. 12, 2006, and a continuation of application No. 10/338,943, filed on Jan. 8, 2003, now Pat. No. 7,163,526.

(30) Foreign Application Priority Data

Jun. 11, 2002   (SG) ............................. 200206693-4

(51) Int. Cl.
*A61M 5/178* (2006.01)
*A61M 5/158* (2006.01)
*A61M 5/162* (2006.01)

(52) U.S. Cl.
USPC ................. 604/168.01; 604/244; 604/260

(58) Field of Classification Search
USPC ............. 604/168.01, 244, 260; 600/576, 578, 600/579
See application file for complete search history.

(56) References Cited

U.S. PATENT DOCUMENTS

| | | |
|---|---|---|
| 1,779,451 A | 10/1930 | Sponsel |
| 2,004,050 A | 6/1935 | Kerk |
| 2,700,385 A | 1/1955 | Ortiz |
| 2,836,942 A | 6/1958 | Miskel |
| 2,854,976 A | 10/1958 | Heydrich |
| 2,953,243 A | 9/1960 | Roehr |
| 3,021,942 A | 2/1962 | Hamilton |
| 3,073,307 A | 1/1963 | Stevens |
| 3,074,542 A | 1/1963 | Myerson et al. |
| 3,255,873 A | 6/1966 | Speelman |
| 3,294,231 A | 12/1966 | Vanderbeck |
| 3,323,523 A | 6/1967 | Scislowicz et al. |
| 3,329,146 A | 7/1967 | Waldman, Jr. |

(Continued)

FOREIGN PATENT DOCUMENTS

| | | |
|---|---|---|
| DE | 3932112 C2 | 9/1999 |
| EP | 0060385 A1 | 9/1982 |

(Continued)

*Primary Examiner* — Emily Schmidt
*Assistant Examiner* — Michael J Anderson
(74) *Attorney, Agent, or Firm* — The Webb Law Firm

(57) ABSTRACT

A needle assembly is provided with the housing, and IV cannula for accessing a blood vessel and a non-patient cannula for communication with an evacuated tube. A flashback chamber is provided in the housing at or near the distal end of the housing. A shield is hinged to a portion of the assembly proximally of the entrance to the flashback chamber. As a result, good visibility of the flashback chamber is achieved. After use, the shield can be rotated into a closed portion for surrounding the IV cannula and avoiding accidental needle sticks.

21 Claims, 5 Drawing Sheets

(56) References Cited

U.S. PATENT DOCUMENTS

| | | |
|---|---|---|
| 3,333,682 A | 8/1967 | Burke |
| 3,367,488 A | 2/1968 | Hamilton |
| 3,382,865 A | 5/1968 | Worrall, Jr. |
| 3,485,239 A | 12/1969 | Vanderbeck |
| 3,537,452 A | 11/1970 | Wilks |
| 3,585,984 A | 6/1971 | Buchanan |
| 3,610,240 A | 10/1971 | Harautuneian |
| 3,658,061 A | 4/1972 | Hall |
| 3,664,879 A | 5/1972 | Olsson |
| 3,817,240 A | 6/1974 | Ayres |
| 3,828,775 A | 8/1974 | Armel |
| 3,859,998 A | 1/1975 | Thomas et al. |
| 3,874,367 A | 4/1975 | Ayres |
| 3,886,930 A | 6/1975 | Ryan |
| 3,890,971 A | 6/1975 | Leeson et al. |
| 3,904,033 A | 9/1975 | Haerr |
| 3,934,722 A | 1/1976 | Goldberg |
| 3,968,876 A | 7/1976 | Brookfield |
| 4,106,497 A | 8/1978 | Percarpio |
| 4,108,175 A | 8/1978 | Orton |
| 4,113,090 A | 9/1978 | Carstens |
| 4,139,009 A | 2/1979 | Alvarez |
| 4,140,108 A | 2/1979 | Nugent |
| 4,154,229 A | 5/1979 | Nugent |
| 4,166,450 A | 9/1979 | Abramson |
| 4,175,008 A | 11/1979 | White |
| 4,193,400 A | 3/1980 | Loveless et al. |
| 4,207,870 A | 6/1980 | Eldridge |
| 4,269,186 A | 5/1981 | Loveless et al. |
| 4,300,678 A | 11/1981 | Gyure et al. |
| 4,305,406 A | 12/1981 | Megahed |
| 4,312,362 A | 1/1982 | Kaufman |
| 4,317,445 A | 3/1982 | Robinson |
| 4,340,068 A | 7/1982 | Kaufman |
| RE31,086 E | 11/1982 | Johnson, Jr. et al. |
| 4,375,849 A | 3/1983 | Hanifl |
| 4,385,637 A | 5/1983 | Akhavi |
| 4,398,544 A | 8/1983 | Nugent et al. |
| 4,409,990 A | 10/1983 | Mileikowsky |
| 4,412,548 A | 11/1983 | Hoch |
| 4,416,290 A | 11/1983 | Lutkowski |
| 4,416,291 A | 11/1983 | Kaufman |
| 4,418,703 A | 12/1983 | Hoch et al. |
| 4,430,082 A | 2/1984 | Schwabacher |
| 4,436,098 A | 3/1984 | Kaufman |
| 4,444,203 A | 4/1984 | Engelman |
| RE31,700 E | 10/1984 | Yamaguchi |
| 4,573,976 A | 3/1986 | Sampson et al. |
| 4,592,744 A | 6/1986 | Jagger et al. |
| 4,617,941 A | 10/1986 | Ichikawa et al. |
| 4,634,428 A | 1/1987 | Cuu |
| 4,641,663 A | 2/1987 | Juhn |
| 4,643,722 A | 2/1987 | Smith, Jr. |
| 4,650,468 A | 3/1987 | Jennings, Jr. |
| 4,659,330 A | 4/1987 | Nelson et al. |
| 4,664,249 A | 5/1987 | Gherardi |
| 4,664,259 A | 5/1987 | Landis |
| 4,664,654 A | 5/1987 | Strauss |
| 4,671,408 A | 6/1987 | Raines et al. |
| 4,675,017 A | 6/1987 | Sato |
| 4,679,571 A * | 7/1987 | Frankel et al. ............ 600/577 |
| 4,681,567 A | 7/1987 | Masters et al. |
| 4,695,274 A | 9/1987 | Fox |
| 4,702,738 A | 10/1987 | Spencer |
| 4,723,943 A | 2/1988 | Spencer |
| 4,728,320 A | 3/1988 | Chen |
| 4,728,321 A | 3/1988 | Chen |
| 4,731,059 A | 3/1988 | Wanderer et al. |
| 4,735,311 A | 4/1988 | Lowe et al. |
| 4,735,618 A | 4/1988 | Hagen |
| 4,737,144 A | 4/1988 | Choksi |
| 4,738,663 A | 4/1988 | Bogan |
| 4,743,233 A | 5/1988 | Schneider |
| 4,746,008 A | 5/1988 | Heverly et al. |
| 4,747,836 A | 5/1988 | Luther |
| 4,747,837 A | 5/1988 | Hauck |
| 4,772,272 A | 9/1988 | McFarland |
| 4,778,453 A | 10/1988 | Lopez |
| 4,781,697 A | 11/1988 | Slaughter |
| 4,782,841 A | 11/1988 | Lopez |
| 4,788,986 A | 12/1988 | Harris |
| 4,790,828 A | 12/1988 | Dombrowski et al. |
| 4,793,484 A | 12/1988 | Schoettle |
| 4,795,432 A | 1/1989 | Karczmer |
| 4,795,443 A | 1/1989 | Permenter et al. |
| 4,801,295 A | 1/1989 | Spencer |
| 4,803,999 A | 2/1989 | Liegner |
| 4,804,372 A | 2/1989 | Laico et al. |
| 4,813,426 A | 3/1989 | Haber et al. |
| 4,816,022 A | 3/1989 | Poncy |
| 4,816,024 A | 3/1989 | Sitar et al. |
| 4,819,659 A | 4/1989 | Sitar |
| 4,820,277 A | 4/1989 | Norelli |
| 4,826,490 A | 5/1989 | Byrne et al. |
| 4,826,491 A | 5/1989 | Schramm |
| 4,838,871 A | 6/1989 | Luther |
| 4,840,619 A | 6/1989 | Hughes |
| 4,842,587 A | 6/1989 | Poncy |
| 4,844,089 A | 7/1989 | Roberti |
| 4,846,796 A | 7/1989 | Carrell et al. |
| 4,850,968 A | 7/1989 | Romano |
| 4,850,976 A | 7/1989 | Heinrich et al. |
| 4,850,977 A | 7/1989 | Bayless |
| 4,850,978 A | 7/1989 | Dudar et al. |
| 4,850,994 A | 7/1989 | Zerbst et al. |
| 4,850,996 A | 7/1989 | Cree |
| 4,858,607 A | 8/1989 | Jordan et al. |
| 4,863,434 A | 9/1989 | Bayless |
| 4,863,435 A | 9/1989 | Sturman et al. |
| 4,863,436 A | 9/1989 | Glick |
| 4,865,592 A | 9/1989 | Rycroft |
| 4,867,746 A | 9/1989 | Dufresne |
| 4,872,552 A | 10/1989 | Unger |
| 4,874,383 A | 10/1989 | McNaughton |
| 4,874,384 A | 10/1989 | Nunez |
| 4,883,469 A | 11/1989 | Glazier |
| 4,886,072 A * | 12/1989 | Percarpio et al. ............ 600/576 |
| 4,886,503 A | 12/1989 | Miller |
| 4,888,001 A | 12/1989 | Schoenberg |
| 4,892,107 A | 1/1990 | Haber |
| 4,892,521 A | 1/1990 | Laico et al. |
| 4,894,052 A | 1/1990 | Crawford |
| 4,894,055 A | 1/1990 | Sudnak |
| 4,900,307 A | 2/1990 | Kulli |
| 4,900,309 A | 2/1990 | Netherton et al. |
| 4,909,791 A | 3/1990 | Norelli |
| 4,909,792 A | 3/1990 | Norelli |
| 4,917,671 A | 4/1990 | Chang |
| 4,921,096 A | 5/1990 | McFarlane |
| 4,927,018 A | 5/1990 | Yang et al. |
| 4,944,397 A | 7/1990 | Miller |
| 4,966,591 A | 10/1990 | Yuen |
| 4,971,068 A | 11/1990 | Sahi |
| 4,976,699 A | 12/1990 | Gold |
| 4,982,842 A * | 1/1991 | Hollister ............ 206/365 |
| 4,994,046 A | 2/1991 | Wesson et al. |
| 5,011,475 A | 4/1991 | Olson |
| 5,011,479 A | 4/1991 | Le et al. |
| 5,015,241 A | 5/1991 | Feimer |
| 5,030,207 A | 7/1991 | Mersch et al. |
| 5,032,116 A | 7/1991 | Peterson et al. |
| 5,033,476 A | 7/1991 | Kasai |
| 5,046,509 A | 9/1991 | Kater |
| 5,055,102 A | 10/1991 | Sitnik |
| 5,069,225 A | 12/1991 | Okamura |
| 5,078,693 A | 1/1992 | Shine |
| 5,078,698 A | 1/1992 | Stiehl et al. |
| 5,092,845 A | 3/1992 | Chang |
| 5,112,327 A | 5/1992 | Iinuma et al. |
| 5,116,325 A | 5/1992 | Paterson |
| 5,120,319 A | 6/1992 | Van Heugten et al. |
| 5,122,121 A | 6/1992 | Sos et al. |
| 5,125,414 A | 6/1992 | Dysarz |
| 5,135,509 A | 8/1992 | Olliffe |

(56) References Cited

U.S. PATENT DOCUMENTS

| | | |
|---|---|---|
| 5,137,518 A | 8/1992 | Mersch |
| 5,139,489 A | 8/1992 | Hollister |
| 5,151,089 A | 9/1992 | Kirk, III et al. |
| 5,154,285 A | 10/1992 | Hollister |
| 5,181,523 A | 1/1993 | Wendelborn |
| 5,188,611 A | 2/1993 | Orgain |
| 5,195,985 A | 3/1993 | Hall |
| 5,197,954 A | 3/1993 | Cameron |
| 5,201,794 A | 4/1993 | Kasai et al. |
| 5,207,653 A | 5/1993 | Janjua et al. |
| 5,215,534 A | 6/1993 | De Harde et al. |
| 5,217,025 A | 6/1993 | Okamura |
| 5,222,502 A * | 6/1993 | Kurose ................. 600/576 |
| 5,232,454 A | 8/1993 | Hollister |
| 5,232,455 A | 8/1993 | Hollister |
| 5,242,411 A | 9/1993 | Yamamoto et al. |
| 5,242,417 A | 9/1993 | Paudler |
| 5,256,153 A | 10/1993 | Hake |
| 5,277,311 A | 1/1994 | Hollister |
| 5,290,246 A | 3/1994 | Yamamoto et al. |
| 5,295,969 A | 3/1994 | Fischell et al. |
| 5,295,970 A | 3/1994 | Clinton et al. |
| 5,303,713 A | 4/1994 | Kurose |
| 5,306,259 A | 4/1994 | Fischell et al. |
| 5,312,369 A | 5/1994 | Arcusin et al. |
| 5,312,372 A | 5/1994 | DeHarde et al. |
| 5,336,199 A | 8/1994 | Castillo et al. |
| 5,348,544 A | 9/1994 | Sweeney et al. |
| 5,356,392 A | 10/1994 | Firth et al. |
| 5,401,251 A | 3/1995 | Hui |
| 5,405,332 A | 4/1995 | Opalek |
| 5,411,480 A | 5/1995 | Kriesel |
| 5,411,492 A | 5/1995 | Sturman et al. |
| 5,419,770 A | 5/1995 | Crass et al. |
| 5,423,765 A | 6/1995 | Hollister |
| 5,439,449 A | 8/1995 | Mapes et al. |
| 5,450,856 A | 9/1995 | Norris |
| 5,462,534 A | 10/1995 | Debreczeni |
| 5,466,223 A | 11/1995 | Bressler et al. |
| 5,485,854 A | 1/1996 | Hollister |
| 5,486,163 A | 1/1996 | Haynes |
| 5,490,841 A | 2/1996 | Landis |
| 5,496,281 A | 3/1996 | Krebs |
| 5,501,674 A | 3/1996 | Trombley, III et al. |
| 5,501,675 A | 3/1996 | Erskine |
| 5,509,907 A | 4/1996 | Bevilacqua |
| 5,520,193 A | 5/1996 | Suzuki et al. |
| 5,533,984 A | 7/1996 | Parmigiani |
| 5,542,932 A | 8/1996 | Daugherty |
| 5,584,816 A | 12/1996 | Gyure et al. |
| 5,599,313 A | 2/1997 | Gyure et al. |
| 5,599,318 A | 2/1997 | Sweeney et al. |
| 5,603,699 A | 2/1997 | Shine |
| 5,632,732 A | 5/1997 | Szabo et al. |
| 5,643,219 A | 7/1997 | Burns |
| 5,662,617 A * | 9/1997 | Odell et al. ................. 604/192 |
| 5,665,075 A | 9/1997 | Gyure et al. |
| 5,669,889 A | 9/1997 | Gyure et al. |
| 5,672,161 A | 9/1997 | Allen et al. |
| 5,676,658 A | 10/1997 | Erskine |
| 5,693,022 A | 12/1997 | Haynes |
| 5,697,914 A | 12/1997 | Brimhall |
| 5,702,369 A | 12/1997 | Mercereau |
| 5,704,920 A | 1/1998 | Gyure |
| 5,733,265 A | 3/1998 | Bachman et al. |
| 5,749,857 A | 5/1998 | Cuppy |
| 5,755,701 A | 5/1998 | Sarstedt |
| 5,807,351 A | 9/1998 | Kashmer |
| 5,830,190 A | 11/1998 | Howell |
| 5,836,920 A | 11/1998 | Robertson |
| 5,885,249 A | 3/1999 | Irisawa |
| 5,893,844 A | 4/1999 | Misawa |
| 5,913,846 A * | 6/1999 | Szabo ................. 604/263 |
| 5,935,110 A | 8/1999 | Brimhall |
| 5,957,892 A | 9/1999 | Thorne |
| 5,984,895 A | 11/1999 | Padilla et al. |
| 5,984,899 A | 11/1999 | D'Alessio et al. |
| 5,993,426 A | 11/1999 | Hollister |
| 6,024,727 A | 2/2000 | Thorne et al. |
| D422,700 S | 4/2000 | Crawford et al. |
| 6,059,737 A | 5/2000 | Crawford |
| 6,077,244 A | 6/2000 | Botich et al. |
| 6,077,253 A | 6/2000 | Cosme |
| 6,080,137 A | 6/2000 | Pike |
| 6,096,006 A | 8/2000 | Sarstedt et al. |
| 6,110,160 A | 8/2000 | Farber |
| 6,113,555 A | 9/2000 | Parmigiani |
| 6,120,482 A | 9/2000 | Szabo |
| 6,139,533 A | 10/2000 | Xia et al. |
| 6,149,629 A | 11/2000 | Wilson et al. |
| 6,156,010 A | 12/2000 | Kuracina et al. |
| 6,190,370 B1 | 2/2001 | Tsui |
| 6,197,007 B1 | 3/2001 | Thorne et al. |
| D442,280 S | 5/2001 | Crawford et al. |
| 6,228,067 B1 | 5/2001 | Gabriel |
| RE37,252 E | 7/2001 | Hollister |
| 6,254,575 B1 | 7/2001 | Thorne, Jr. et al. |
| 6,261,263 B1 | 7/2001 | Huet et al. |
| 6,298,541 B1 | 10/2001 | Newby et al. |
| 6,319,232 B1 | 11/2001 | Kashmer |
| 6,328,713 B1 | 12/2001 | Hollister |
| 6,334,857 B1 | 1/2002 | Hollister et al. |
| 6,436,086 B1 | 8/2002 | Newby et al. |
| 6,440,104 B1 | 8/2002 | Newby et al. |
| 6,533,760 B2 | 3/2003 | Leong |
| 6,712,792 B2 | 3/2004 | Leong |
| 7,160,267 B2 | 1/2007 | Brown |
| 7,163,526 B2 | 1/2007 | Leong et al. |
| 7,226,432 B2 | 6/2007 | Brown |
| 7,396,343 B2 | 7/2008 | Brown |
| 7,530,967 B2 | 5/2009 | Brown |
| 2001/0044847 A1 | 11/2001 | Kirchhofer et al. |
| 2002/0188256 A1 | 12/2002 | Crawford et al. |
| 2002/0193655 A1 | 12/2002 | Cocker et al. |
| 2008/0319346 A1 * | 12/2008 | Crawford et al. ............. 600/577 |
| 2009/0204026 A1 * | 8/2009 | Crawford et al. ............. 600/576 |
| 2011/0166474 A1 * | 7/2011 | Crawford et al. ............. 600/576 |
| 2011/0166475 A1 * | 7/2011 | Crawford et al. ............. 600/576 |
| 2011/0166476 A1 * | 7/2011 | Crawford et al. ............. 600/579 |
| 2011/0178427 A1 * | 7/2011 | Tan et al. ................. 600/578 |

FOREIGN PATENT DOCUMENTS

| | | |
|---|---|---|
| EP | 0139872 A1 | 5/1985 |
| EP | 0321358 B1 | 6/1989 |
| EP | 0376168 A2 | 7/1990 |
| EP | 0486840 B1 | 10/1991 |
| EP | 0462702 B1 | 2/1994 |
| EP | 0619096 A1 | 10/1994 |
| EP | 0478459 B1 | 7/1996 |
| EP | 0848441 A1 | 6/1998 |
| GB | 1233302 A | 5/1971 |
| GB | 2239604 A | 7/1991 |
| GB | 2239607 A | 7/1991 |
| GB | 2240273 A | 7/1991 |
| GB | 2240477 A | 8/1991 |
| JP | 58183172 | 10/1983 |
| JP | 58188460 | 11/1983 |
| JP | 58212454 | 12/1983 |
| JP | 04132541 A | 5/1992 |
| JP | 04364831 A | 12/1992 |
| JP | 06007330 A | 1/1994 |
| JP | 7013304 | 1/1995 |
| JP | 07039541 A | 2/1995 |
| JP | 0739804 U | 7/1995 |
| JP | 08150134 A | 6/1996 |
| JP | 08257018 A | 10/1996 |
| JP | 08275933 A | 10/1996 |
| JP | 11028200 A | 2/1999 |
| JP | 11169359 A | 6/1999 |
| JP | 200023948 | 1/2000 |
| JP | 2000139879 | 5/2000 |
| JP | 2000166903 | 6/2000 |
| JP | 2001000424 | 1/2001 |

(56) References Cited

FOREIGN PATENT DOCUMENTS

| | | |
|---|---|---|
| JP | 2001299728 | 10/2001 |
| JP | 2001299729 A | 10/2001 |
| WO | 8707162 A1 | 12/1987 |
| WO | 9001348 A1 | 2/1990 |
| WO | 9109637 A1 | 7/1991 |
| WO | 9109638 A1 | 7/1991 |
| WO | 9109639 A2 | 7/1991 |
| WO | 9316745 A1 | 9/1993 |
| WO | 96/29107 A1 | 9/1996 |
| WO | 98/56825 A1 | 12/1998 |
| WO | 99/03417 | 1/1999 |
| WO | 99/23947 A1 | 5/1999 |

\* cited by examiner

FLASHBACK BLOOD COLLECTION NEEDLE WITH NEEDLE SHIELD

CROSS-REFERENCE TO RELATED APPLICATIONS

This application is a continuation of U.S. patent application Ser. No. 11/609,702 entitled "Flashback Blood Collection Needle with Needle Shield", filed Dec. 12, 2006, which is a continuation application of U.S. patent application Ser. No. 10/338,943, filed Jan. 8, 2003, which in turn claims priority to Singapore Patent Application No. 200206693-4, filed Jun. 11, 2002, the entire disclosures of each of which are hereby incorporated by reference.

BACKGROUND OF THE INVENTION

1. Field of the Invention

A shieldable blood collection needle assembly with a flashback chamber for providing confirmation of venous entry.

2. Description of Related Art

Needle assemblies are used for collecting specimens of fluid, such as blood, from a patient. Some such needle assemblies are intended for use with an evacuated tube, such as tubes sold under the trademark VACUTAINER™ by Becton, Dickinson and Company. Needle assemblies for use with an evacuated fluid collection tube include a needle hub with a proximal end, a distal end and a passage extending between the ends. The needle assembly further includes at least one needle cannula mounted to the needle hub. The needle cannula includes a sharply pointed distal end that projects distally beyond the needle hub, a proximal end that projects proximally beyond the needle hub and a lumen that provides communication between the opposed ends of the needle cannula. Some needle assemblies include separate proximal and distal cannulas and rely upon a portion of the needle hub to provide communication between the lumens of the respective cannulas. The distal end of the needle cannula typically is beveled to a tip that is sufficiently sharp for piercing the skin of the patient and accessing the vein or other source of fluid that is to be collected. The proximal end of the needle cannula is configured for piercing the rubber stopper on an evacuated tube. The proximal end of the needle cannula typically is covered by a needle pierceable resealable multi-sample sleeve. The sleeve is compressed by the rubber stopper of the evacuated tube and punctured by the proximal end of the needle cannula as the proximal end of the needle cannula is urged into communication with the evacuated tube.

One problem with collecting fluid from a patient relates to uncertainty during attempts to access the proper source of fluid in the patient. For example, a blood collection procedure typically requires the phlebotomist to visually locate a vein and then to enter the vein with the distal end of the needle cannula. The phlebotomist may not have a positive indication of venous entry at this stage. An evacuated tube then is placed in communication with the proximal end of the needle cannula once the phlebotomist is reasonably certain that the targeted blood vessel has been entered. The low pressure within the evacuated tube then cooperates with the higher pressure of the blood to generate a flow of blood into the tube. The flow of blood into the tube may be the first positive indication to the phlebotomist that the targeted blood vessel has been accessed. The initial flow of blood along the long needle cannula and into the evacuated tube may take a relatively long time based on several factors, including the relative pressure levels and the length and cross-sectional dimensions of the needle cannula. The phlebotomist may interpret the absence of an immediate flow of blood as being a sign that the blood vessel was not targeted properly, when in fact the absence of a visible blood flow in the evacuated tube may be attributable to pressure and fluid flow characteristics. Thus, the phlebotomist may unnecessarily withdraw the needle and start the blood collection procedure again. As a result, time is wasted and trauma for the patient is increased. In view of the above problems, many fluid collection needle assemblies are provided with a flashback chamber that communicates with the needle cannula. The flashback chamber typically is formed at least partly from a transparent or translucent material and is intended to receive a portion of the blood flow shortly after a vein has been accessed properly.

The blood collection needle assembly is withdrawn from the patient after a suitable number of samples have been collected. The used needle assembly then is discarded. The medical profession is well aware that accidental sticks with a used needle cannula can transmit disease. Accordingly, it is desirable to shield the used needle cannula immediately after the needle cannula has been withdrawn from the patient. Shields have taken many different forms. For example, some shields telescope in a distal to proximal direction over the needle cannula and frictionally engage the needle hub. Shields of this type create the risk of an accidental needle stick during shielding if the shield is misaligned with the needle cannula. Some shields of this general type are provided with enlarged collars that are intended to minimize the risk of accidental sticks during shielding. However, shields of this general type are not preferred. Other shields are telescoped over the needle hub and can be moved distally over the needle cannula to effect shielding. Shields of this general type are safe and effective and are used in many situations. However, shields of this type can interfere with the normal usage of some medical implements. Other shields are hingedly mounted to or near the needle hub and can be rotated from an open position where the needle cannula is exposed to a closed position where the needle cannula is shielded. Shields of this type also work very well and are widely accepted. However, the existence of a hinged shield on a fluid collection needle assembly with a flashback chamber is intuitively problematic in view of the complexities of providing both shielding and an unobstructed view of the flashback chamber.

SUMMARY OF THE INVENTION

The subject invention is directed to a shieldable fluid collection needle assembly. The needle assembly includes a housing with a proximal end wall, a distal end wall and an external sidewall extending between the proximal and distal end walls such that a chamber is defined between the end walls and the external sidewall. The external sidewall may be formed unitarily with at least one of the end walls. Additionally, at least a portion of the external sidewall is formed from a transparent or translucent material so that the interior of the chamber within the housing is visible. A proximal passage extends through the proximal end wall of the housing and a distal passage extends through the distal end wall of the housing. The proximal and distal passages maybe axially aligned with one another. The housing may further include an internal sidewall extending proximally from the distal end wall and surrounding the entry of the distal passage into the chamber. The internal sidewall also is a transparent or translucent material.

The needle assembly further includes a distal cannula mounted in the distal passage of the housing and projecting distally beyond the housing. The distal cannula includes a distal end spaced externally from the housing. The distal end may be beveled to a tip that is sufficiently sharp to pierce skin of a patient. The distal cannula includes a lumen that extends from the distal end of the distal cannula and communicates with the chamber of the housing.

The needle assembly further includes a proximal cannula mounted in the proximal passage of the housing. The proximal cannula includes a proximal end that projects proximally beyond the housing. Additionally, the proximal cannula includes a lumen that extends from the proximal end and into communication with the chamber. The proximal cannula also includes a distal end that may extend into the chamber so that the proximal end of the distal cannula and the distal end of the proximal cannula substantially align with one another and are slightly spaced from one another. In an alternate embodiment, distal and proximal cannula may be integral with one another and may include a transverse slot or aperture to provide communication between the lumens of the distal and proximal cannulas with the chamber in the housing.

The proximal end of the distal cannula preferably is at or near the distal end wall of the housing. Additionally, the distal end of the proximal cannula preferably extends through a major portion of the chamber of the housing and to a location near the distal end wall of the housing. Thus, both the distal and proximal cannulas preferably communicate with the chamber of the needle assembly at a location near the distal end wall of the housing. As a result, the first indication of fluid flow through the distal cannula will occur at a location at or substantially adjacent the distal end wall of the housing. In a preferred embodiment, the housing may have the internal sidewall described above and the distal end of the proximal cannula may project axially into the cylindrical space bounded by the internal sidewall.

The needle assembly of the subject invention further includes a shield that may be hinged to a location on the housing proximally of the location where the first indication of flashback occurs. The shield initially is in an open position where the shield is spaced from the distal cannula and the chamber. Hence, the shield does not impede usage of the distal cannula or visual observation of the chamber when the shield is in its open position. However, the shield can be rotated from the open position to a closed position where the shield surrounds the distal cannula. The shield and/or the housing may include at least one locking element for locking the shield in the closed position. The locking means can include a resiliently deflectable cannula lock configured for engaging the needle cannula when the shield is in the closed position. The shield may further include locks for engaging structure on the housing when the shield is in the closed position. The engagement between structure on the shield and structure on the housing may function to lock the shield in the closed position. Alternatively, primary locking of the shield in the closed position may be achieved by the cannula lock, and the engagement between the shield and the housing may be provided primarily for audible and tactile indication of complete shielding.

DETAILED DESCRIPTION

Figure 1:
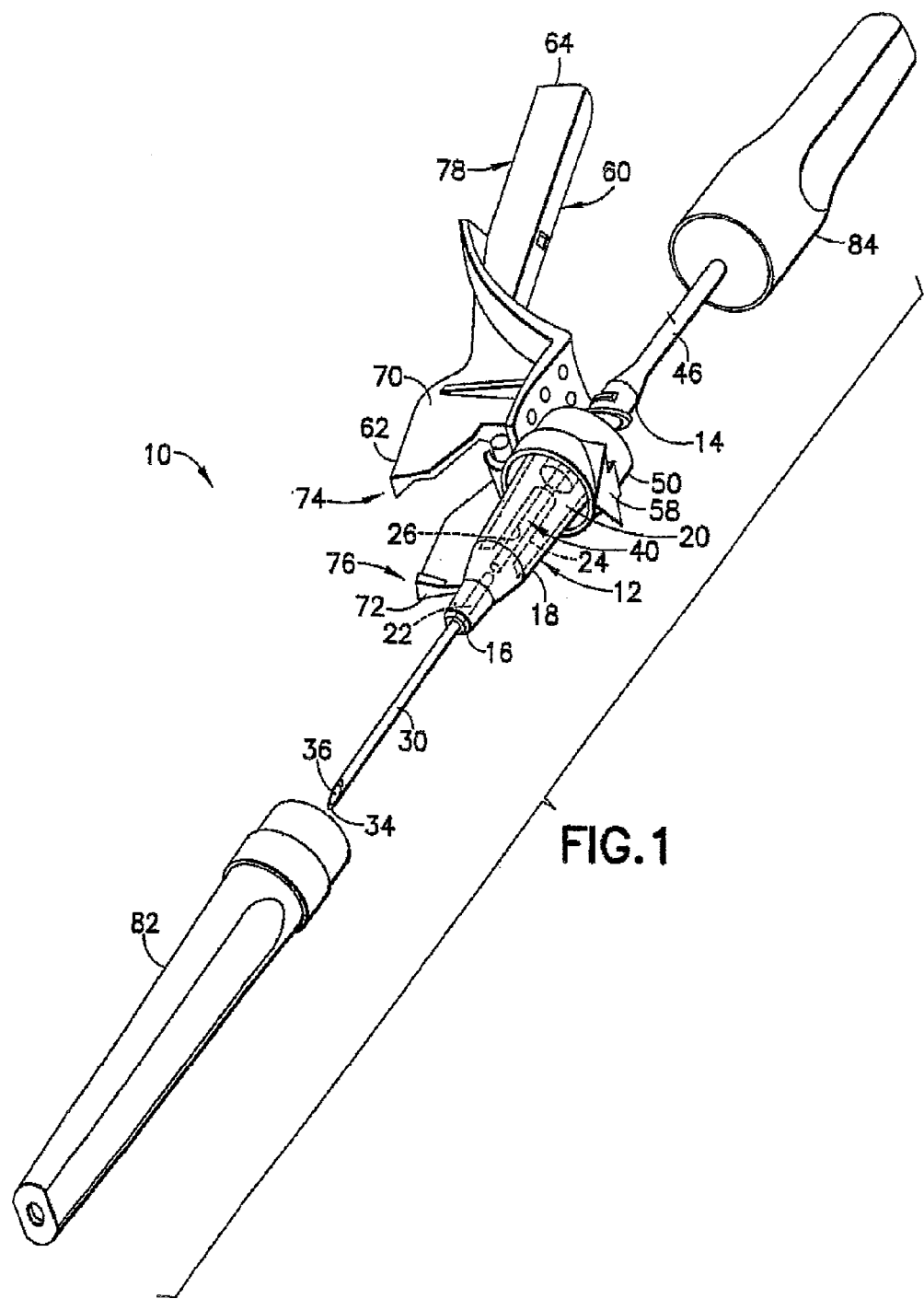
FIG. 1 is an exploded perspective view of a needle assembly in accordance with the invention.
Figure 2:
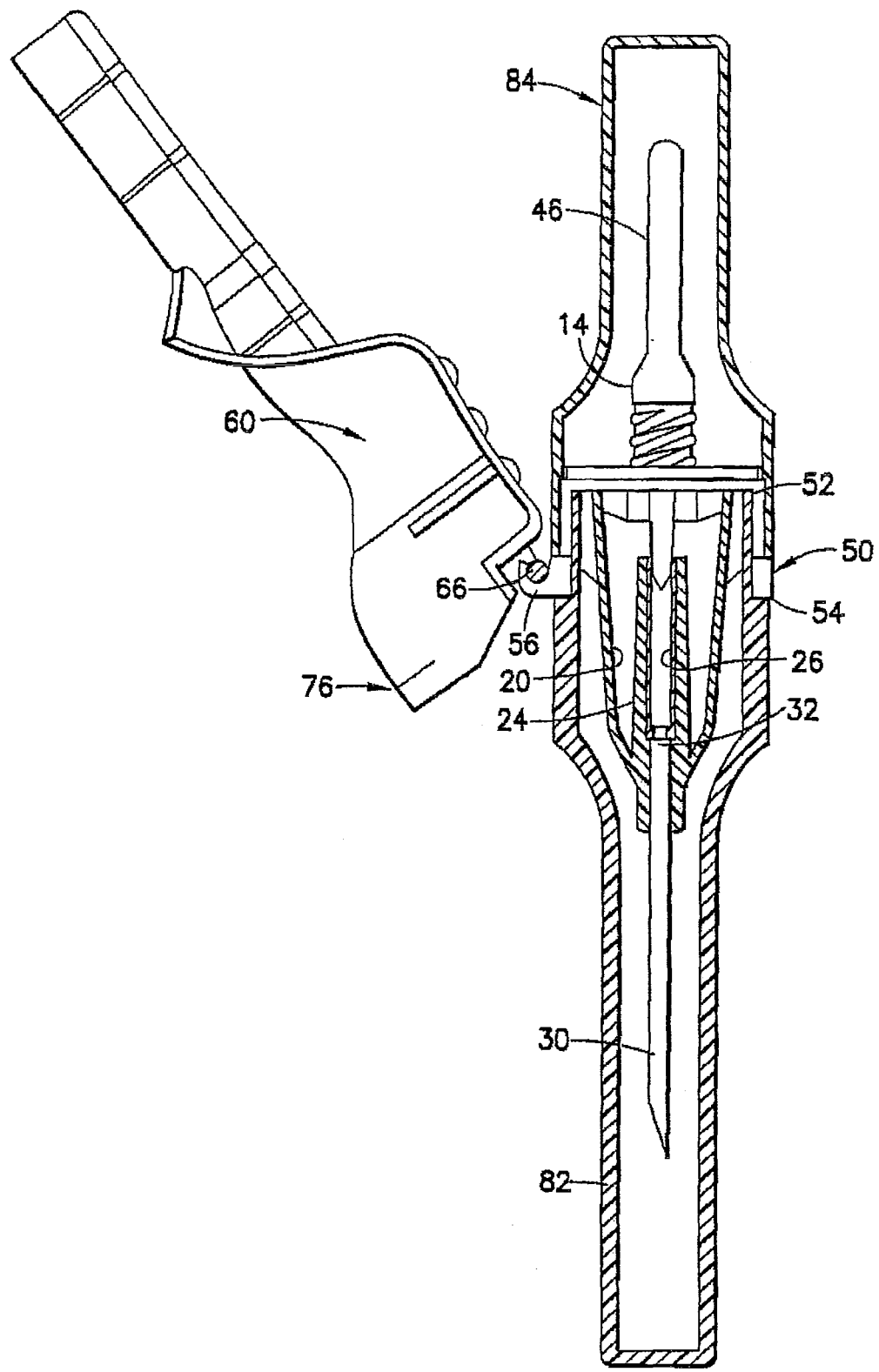
FIG. 2 is a longitudinal cross-sectional view of the needle assembly prior to use.
Figure 3:
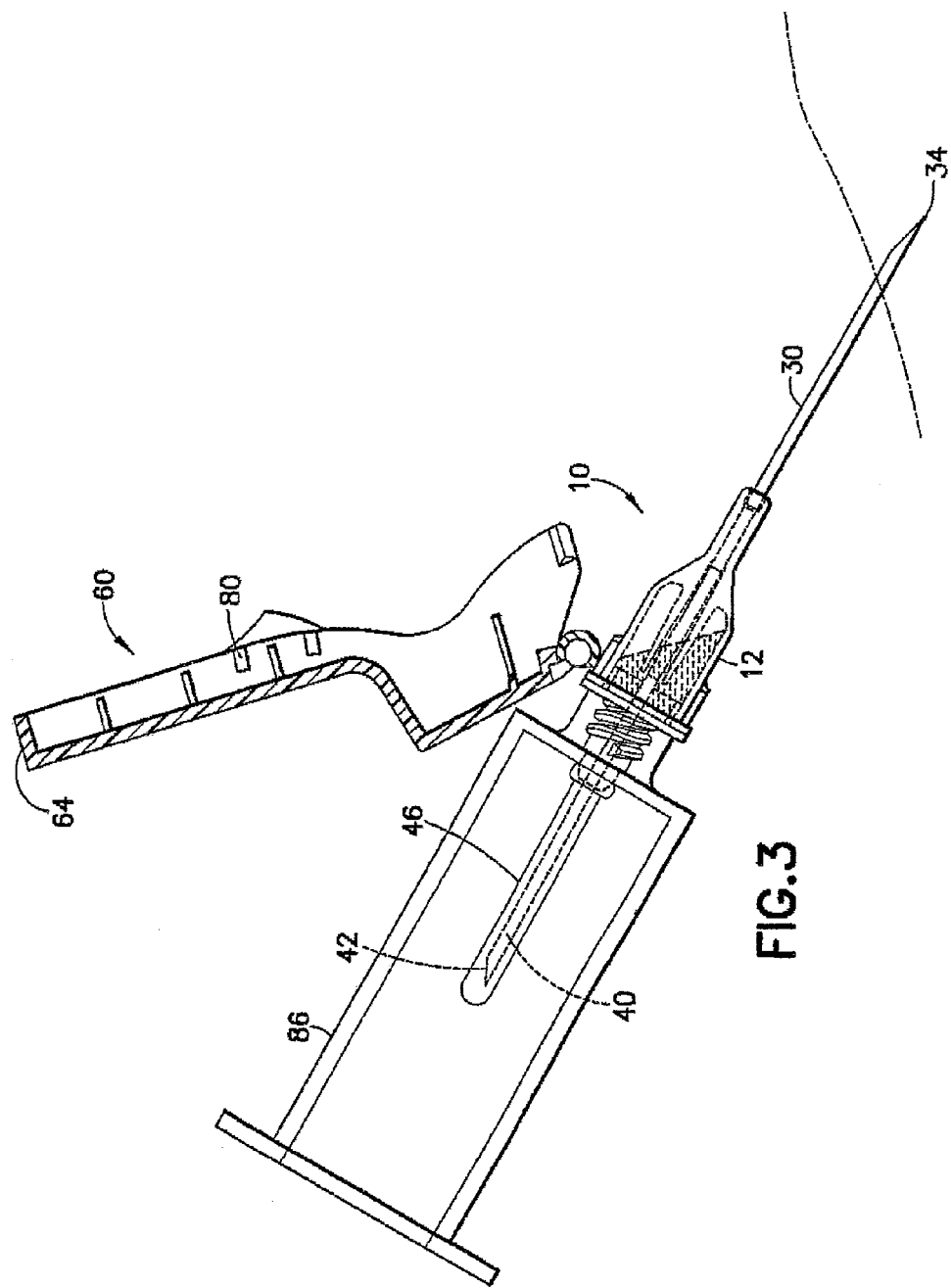
FIG. 3 is a side elevational view of the needle assembly after being placed in communication with a blood vessel, but before being placed in communication with an evacuated tube.
Figure 4:
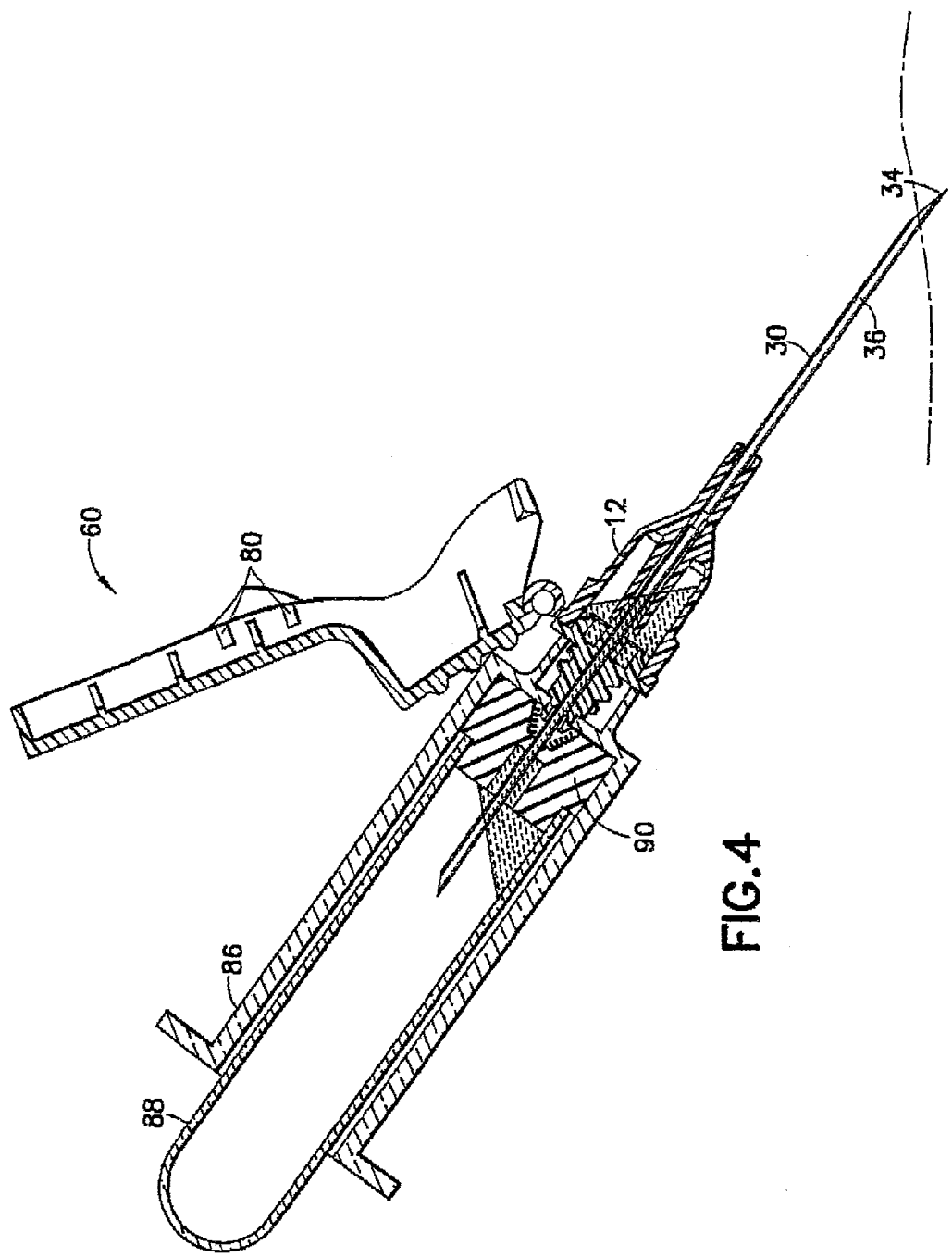
FIG. 4 is a longitudinal cross-sectional view of the needle assembly during use and after being placed in communication with an evacuated tube.

A needle assembly in accordance with the subject invention is identified generally by the numeral 10 in FIGS. 1-5. Needle assembly 10 includes a housing 12 with a proximal end 14, a distal end 16 and a generally frustum-shaped outer sidewall 18 extending between the ends. Outer sidewall 18 is formed from a transparent or translucent plastic material and defines a chamber 20 within housing 12 between proximal end 14 and distal end 16. A proximal passage (not shown) extends through proximal end 14 of housing 12 and communicates with chamber 20. A distal passage 22 extends through distal end 16 of housing 12 and also communicates with chamber 20. Housing 12 further includes a cylindrical inner sidewall 24 that extends from distal end 16 toward proximal end 14. Inner sidewall 24 is substantially concentrically disposed within outer sidewall 18 and is substantially concentrically generated about distal passage 22. Inner sidewall 24 also is formed from a transparent or translucent plastic material. Hence, a fluid material in a portion of chamber 20 bounded by inner sidewall 24 is readily visible from locations externally of outer sidewall 18. Thus, inner sidewall 24 in this embodiment defines a flashback chamber 26, and fluid collected in flashback chamber 26 can be observed from locations externally of needle assembly 10. Chamber 26 communicates with chamber 20, and hence chamber 20 may also contribute to an indication of flashback.

Needle assembly 10 further includes an IV cannula 30 with a proximal end 32, a distal end 34 and a lumen 36 extending between the ends. Distal end 34 of IV cannula 30 is disposed externally of housing 12 and is beveled to a sufficiently sharp tip for piercing skin and tissue of a patient. IV cannula 30 is mounted in distal passage 22 of housing 12 so that proximal end 32 of IV cannula 30 is substantially adjacent distal end 16 of housing 12. Thus, lumen 36 through IV cannula 30 communicates with flashback chamber 26 at a location substantially adjacent distal end 16 of housing 12.

Needle assembly 10 further includes a non-patient (NP) cannula 40 mounted in the proximal passage at proximal end 14 of housing 12. NP cannula 40 includes a proximal end 42 disposed externally of housing 12, a distal end 44 disposed in flashback chamber 26 and a lumen (not shown) extending between the ends. The proximal end 42 is beveled to a sufficiently sharp tip for piercing a rubber stopper of an evacuated tube as explained further herein. The lumen through NP cannula 40 is aligned substantially axially with lumen 36 through IV cannula 30. Distal end 44 of NP cannula 40 preferably is spaced only a short distance from proximal end 32 of IV cannula 30, such as 0.5 mm-1.2 mm.

Needle assembly 10 further includes a sleeve 46 mounted over portions of NP cannula 40 that are disposed externally of housing 12. Sleeve 46 is mounted to proximal end 14 of housing 12, and is formed from a material that is substantially impervious to liquid and fluid. However, sleeve 46 also is formed from a material that is readily pierceable by proximal end 42 of NP cannula 40 and that is resiliently resealable. Thus, the rubber stopper of an evacuated tube can be urged against sleeve 46 and will cause sleeve 46 to collapse distally. As a result, the beveled tip at proximal end 42 of NP cannula 40 will pierce through sleeve 46 and through the rubber stopper on the evacuated tube.

IV cannula 30, NP cannula 40 and housing 12 cooperate to provide an early indication of venous entry due to the flashback of blood in chamber 26 and/or chamber 20 of housing 12. However, other flashback designs can be incorporated into the needle assembly of the subject invention. These other designs include arrangements where blood first fills the equivalent of sleeve 46 on needle assembly 10 and then flows into a flashback chamber. Still other designs include the use of a vented plug. Flashback chamber designs that can be incorporated into the subject invention are shown, for example, in U.S. Pat. No. 5,542,932, U.S. Pat. No. 5,824,001, and others.

Needle assembly 10 further includes a collar 50 securely mounted around proximal portions of housing 12. Collar 50 may be secured mechanically in position on housing 12, may be bonded to housing 12 or may be molded as part of housing 12. Collar 50 includes a proximal end 52 substantially aligned with proximal portions of chamber 20 and a distal end 54 disposed proximally of proximal end 32 of IV cannula 30 and near proximal end of inner sidewall 24. Accordingly, collar 50 will not impair the ability to observe regions of flashback chamber 26 adjacent proximal end 32 of IV cannula 30. Distal end 54 of collar 50 is provided with a C-shaped hook 56 generated about an axis that extends transverse to IV cannula 30 and NP cannula 40. Collar 50 further includes a chevron-shaped projection 58 at a location diametrically opposite hook 56. Collar 50 preferably is secured to housing 12 such that a plane passing symmetrically through C-shaped hook 56 and through the diametrically opposite chevron-shaped projection 58 also passes symmetrically through the bevel at distal end 34 of IV cannula 30. However, in other embodiments collar 50 may be rotatably mounted to housing 12 so that the orientation of the plane passing symmetrically through hook 56 and through projection 58 can be varied relative to a plane passing symmetrically through the bevel at distal end 34 of IV cannula 30.

Needle assembly 10 further includes a shield 60 with a proximal end 62 and a distal end 64. Portions of shield 60 near proximal end 62 include a hinge pin 66 that is snapped into engagement with hook 56 so that shield 60 can rotate relative to hook 56 from an open position shown in FIGS. 1 and 2 to a closed position shown in FIG. 5. In the open position, shield 60 is spaced from IV cannula 30 and is aligned to IV cannula 30 at an obtuse angle of about 120°. The preferred orientation of collar 50 relative to the bevel at distal end 34 of IV cannula 30 provides a clear indication of the preferred bevel-up orientation of IV cannula 30 that is employed by most health care technicians during use. Additionally, the orientation of collar 50 on housing 12 ensures that shield 60 will not interfere with the view of IV cannula 30 during insertion. The above-referenced option of a rotatable collar enables the user to select a preferred orientation of shield 60 relative to the bevel at distal end 34 of IV cannula 30 and relative to the patient and other medical equipment that may be placed in communication with the patient. Portions of shield 60 near proximal end 62 further include a top wall 68 and sidewalls 70 and 72 that project from top wall 68. Portions of sidewalls 70 and 72 at proximal end 62 of shield 60 are spaced apart by a distance that equals or exceeds the width of outer sidewall 18 of housing 12. Thus, sidewalls 70 and 72 easily can be rotated on opposite respective sides of outer sidewall 18 as shield 60 is rotated within hook 56. The wide spacing of sidewalls 70 and 72 also facilitates observations of the flashback chamber 26. Opposed facing surfaces of sidewalls 70 and 72 at proximal end 62 of shield 60 are formed with collar catches 74 and 76 respectively. Collar catches 74 and 76 are configured to snap into engagement with chevron-shaped latch 58 on collar 50. Top wall 68 is provided with an array of tactile bumps on the surface facing away from sidewalls 70 and 72 to provide a visual indication of an actuation landing for a thumb or forefinger and to enhance frictional engagement by the thumb or forefinger when rotating shield 60.

Shield 60 narrows at locations between top wall 68 and distal end 64 and defines a substantially U-shaped channel of sufficient width to receive IV cannula 30. As shown most clearly in FIG. 5, channel 78 is sufficiently long to encompass all of IV needle 30. Interior portions of channel 78 include a resiliently deflectable cannula lock 80 that is angled from one sidewall of channel 78 toward the opposed sidewall and toward the top wall. Cannula lock 80 will yield in response to contact with IV cannula 30 as shield 60 is rotated toward IV cannula 30. Cannula lock 80 is further dimensioned to move passed IV cannula 30 when shield 60 approaches the closed position. Hence, cannula lock 80 will return resiliently toward an undeflected position and will trap IV cannula 30 within shield 60. Although the figures herein depict a single cannula lock 80, plural cannula locks may be provided. Additionally, cannula locks may extend from each of the two sidewalls of U-shaped channel 80. Other structures for locking IV cannula 30 in shield 60 can be provided. These include other configurations for plastic or metal cannula locks that deflect in response to contact with IV cannula 30 and then resiliently move to trap IV cannula 30. Alternatively, the cannula lock may require some form of user activation, such as rotation or axial movement of a portion of the shield.

Needle assembly 10 further includes an IV shield 82 and a NP shield 84 mounted respectively over IV cannula 30 and NP cannula 40 and frictionally retained on collar 50. Shields 82 and 84 can be separated by an appropriate application of pulling and/or slight twisting force.

Needle assembly 10 is used by first separating NP shield 84 from collar 50 and then threading distal end 14 of housing 12 into a needle holder 86. Shield 60 then is rotated into the fully open position shown in FIGS. 1 and 2 where shield 60 is spaced from IV cannula 30 and is aligned to IV cannula 30 at an obtuse angle of about 120°. IV shield 78 then is removed from its engagement with collar 50. The phlebotomist then guides distal end 34 of IV cannula 30 into a targeted blood vessel. A pressure differential between the blood in the vein and the pressure within housing 12 will cause blood to flow through lumen 36 of IV cannula 30. Blood will appear in flashback chamber 26 very quickly after access to the blood vessel has been attained. This blood can be seen in flashback chamber 26 by the phlebotomist due to the disposition and alignment of shield 60 in the open position. The phlebotomist then inserts an evacuated tube 88 into needle holder 82. Evacuated tube 88 includes a rubber stopper 90 that collapses sleeve 46 distally. As a result, proximal end 42 of NP cannula 40 pierces rubber sleeve 46 and then pierces stopper 90 of evacuated tube 88. The phlebotomist accumulates one or more samples of blood in this manner.

Figure 5:
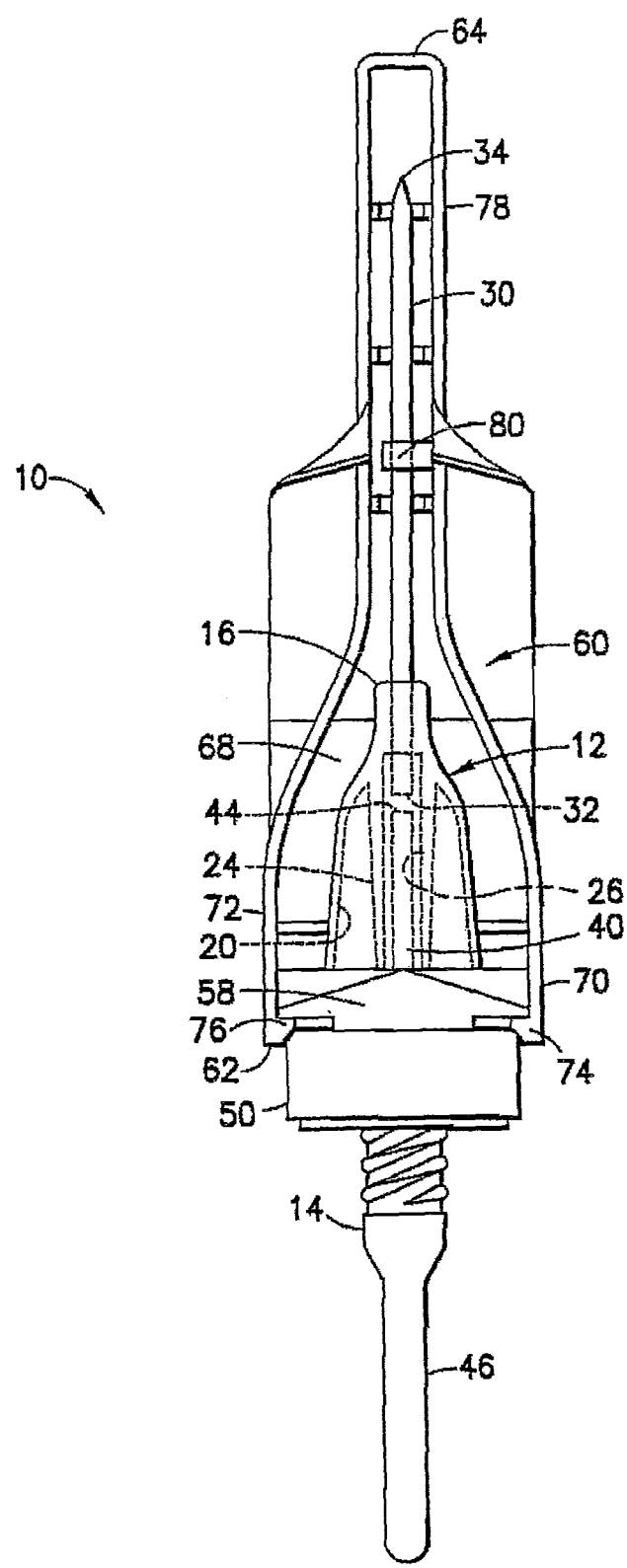
FIG. 5 is a side elevational view of the needle assembly after complete shielding.

After collecting the last sample of blood, the phlebotomist urges needle assembly 10 and needle holder 86 from the patient and immediately exerts pressure with a thumb or forefinger on top wall 68 of shield 60. As a result, shield 60 rotates about hook 56 into a closed position, as shown in FIG. 5, so that IV cannula 30 is surrounded by channel 78 of shield 60. Sufficient rotation causes cannula lock 80 to engage IV cannula 30 and to deflect. Further rotation of shield 60 causes cannula lock 80 to pass IV cannula 30. As a result, cannula lock 80 resiliently returns toward an undeflected condition and traps IV cannula 30. Simultaneously, collar catches 74 and 76 snap into engagement with chevron-shaped latch 58 on collar 50 to provide an audible and tactile indication of shielding. The safely shielded needle assembly then can be discarded in a sharps receptacle.

The needle assembly provides effective shielding without impeding use of needle assembly 10 and without obscuring observation of flashback chamber 26. The high visibility of flashback chamber 26 is partly attributable to the extreme distal position of the space between IV cannula 30 and NP cannula 40 and the corresponding proximal position of shield 60 in the open position. Additionally, as shown most clearly in FIG. 1, proximal end 62 of shield 60 is widely open between sidewalls 70 and 72 to provide a broad range of acceptable viewing angles.

The above-described needle assembly has hinge pin 66 of shield 60 snapped into engagement with C-shaped hook 56 on collar 50 for hinged rotation of shield 60 relative to collar 50 and relative to housing 12. However, other structures for accommodating hinged movement of shield 60 relative to collar 50 and/or housing 12 can be provided. These include forming shield 60 unitarily with collar 50 so that a living hinged connection between shield 60 and collar 50 is provided. A shield with a living hinge is shown, for example, in U.S. Pat. No. 5,681,295. Such hinged connections can also include an over-center hinge where the shield is substantially unbiased in the fully open position and in the fully closed position. However, the user may have to overcome a bias in the over-center hinge during the initial phases of rotation from the open position to the closed position. The over-center hinge then resiliently returns toward an unbiased condition and accelerates the hinge towards the closed position.

What is claimed is:

1. A shieldable needle assembly comprising:
  an assembly including:
    a housing having proximal and distal ends and a chamber wall extending between said ends for defining a chamber in said housing, at least a portion of said chamber wall being formed from a material that permits observation of a fluid flowing into said chamber;
    an IV cannula projecting distally from said housing and communicating with said chamber; and
    a shield pivotable with respect to said assembly and being positionable in an open position where said shield is spaced from said IV cannula and aligned to permit observation of a fluid in said chamber, said shield further being pivotable to a closed position where said shield covers said IV cannula,
  wherein at least a portion of said chamber is disposed distally of a location at which said shield is pivotable with respect to said assembly, and wherein said housing and said IV cannula are configured to provide fluid communication with the chamber for providing an indication of flashback of a fluid flowing into said housing.

2. The shieldable needle assembly of claim 1, wherein said IV cannula communicates with a portion of said chamber adjacent said distal end of said housing, said shield being hingedly connected to a portion of said assembly substantially adjacent said proximal end of said housing.

3. The shieldable needle assembly of claim 1, wherein said shield includes at least one lock for locked engagement with said IV cannula when said shield is in said closed position.

4. The shieldable needle assembly of claim 1, wherein said chamber wall is an outer chamber wall, said housing further comprising an inner chamber wall defining a flashback chamber within said housing, said inner chamber wall extending from said distal end of said housing toward said proximal end of said housing such that said IV cannula communicates with said flashback chamber defined by said inner chamber wall.

5. The shieldable needle assembly of claim 1, wherein said IV cannula has a distal end with a substantially planar bevel defining a tip, said shield being hinged for movement through a plane substantially coincident with a plane of symmetry passing through said bevel at said distal end of said IV cannula.

6. The shieldable needle assembly of claim 1, wherein said shield is hingedly connected to said housing.

7. The shieldable needle assembly of claim 1, wherein said shield is hinged to said housing.

8. A shieldable needle assembly comprising:
  an assembly including:
    a housing having proximal and distal ends and a chamber wall extending between said ends for defining a chamber in said housing, at least a portion of said chamber wall being formed from a material that permits observation of a fluid flowing into said chamber;
    an IV cannula projecting distally from said housing and communicating with said chamber;
    a non-patient cannula projecting from said housing and communicating with said chamber; and
    a shield pivotable with respect to said assembly and being positionable in an open position where said shield is spaced from said IV cannula and aligned to permit observation of a fluid in said chamber, said shield further being pivotable to a closed position where said shield covers said IV cannula,
  wherein said non-patient cannula includes a distal end disposed in said chamber, said distal end of said non-patient cannula being disposed distally of the location at which said shield is pivotable with respect to said assembly and wherein said housing, said IV cannula, and said non-patient cannula are configured to provide fluid communication with the chamber for providing an indication of flashback of a fluid flowing into said housing.

9. The shieldable needle assembly of claim 8, wherein the shield pivotable with respect to said assembly is hingedly connected to said assembly.

10. The shieldable needle assembly of claim 8, wherein the shield pivotable with respect to said assembly is hinged to said assembly.

11. A shieldable assembly comprising:
  a needle holder extending between a first end and a second end and defining an open interior; and
  a needle assembly comprising:
    a housing having proximal and distal ends and a chamber wall extending between said ends for defining a chamber in said housing, at least a portion of said chamber wall being formed from a material that permits observation of a fluid flowing into said chamber, said housing engageable with said first end of said needle holder;
    an intravenous puncture tip extending from said distal end of said housing and a non-patient puncture tip extending from said proximal end of said housing, said non-patient puncture tip extending within said open interior of said needle holder when said housing is engaged with said first end of said needle holder and said intravenous puncture tip in fluid communication with said chamber of said housing; and
    a rotatable shield adapted to be positionable in an open position where said shield is spaced from said intravenous puncture tip, said shield further being rotatable to a closed position where said shield covers said intravenous puncture tip,
  wherein at least a portion of said chamber is disposed distally of a location at which said shield is pivotable with respect to said shieldable assembly so as to permit observation of a fluid in said chamber.

12. The shieldable assembly of claim 11, wherein the needle assembly further comprises a pierceable sleeve encompassing the non-patient puncture tip.

13. The shieldable assembly of claim 11, wherein the needle assembly comprises a first cannula extending from the distal end of the housing defining said intravenous puncture tip.

14. The shieldable assembly of claim 13, wherein the needle assembly further comprises a second cannula extending from the proximal end of the housing defining said non-patient puncture tip.

15. The shieldable assembly of claim 14, wherein the first cannula and the second cannula are separate structures.

16. The shieldable assembly of claim 11, wherein the shield is hingedly connected to said needle assembly.

17. The shieldable assembly of claim 11, wherein the shield is hingedly connected to the housing.

18. The shieldable assembly of claim 11, wherein the shield is hinged to the housing.

19. The shieldable assembly of claim 11, wherein the housing of the needle assembly is engageable with the needle holder such that at least a portion of the chamber wall of the housing that is formed from a material that permits observation of a fluid flowing into said chamber extends from said distal end of the said needle holder.

20. The shieldable assembly of claim 11, wherein the housing of the needle assembly is threadably engaged with an opening extending through the distal end of the needle holder.

21. A shieldable needle assembly comprising:
a housing comprising proximal and distal ends and a sidewall extending therebetween for defining a chamber at least partially disposed between the proximal and distal ends, at least a portion of said chamber wall being formed from a material that permits observation of a fluid flowing into said chamber;
an IV cannula projecting distally from said housing and communicating with said chamber; and
a shield hingedly connected to said assembly and being positionable in an open position where said shield is spaced from said IV cannula and aligned to permit observation of a fluid in said chamber, said shield further being rotatable to a closed position where said shield covers said IV cannula,
wherein at least a portion of said chamber is disposed distally of a location at which said shield is hingedly connected to said assembly, and wherein said housing and said IV cannula are configured to provide fluid communication with the chamber for providing an indication of flashback of a fluid flowing into said housing.

* * * * *